US012653432B2

(12) United States Patent
Shimokawa et al.

(10) Patent No.: US 12,653,432 B2
(45) Date of Patent: Jun. 16, 2026

(54) DEVICE CONTROL APPARATUS, NON-TRANSITORY COMPUTER-READABLE MEDIUM, AND DEVICE CONTROL METHOD

(71) Applicant: Mitsubishi Electric Corporation, Tokyo (JP)

(72) Inventors: Takeaki Shimokawa, Tokyo (JP); Tetsuro Shida, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 357 days.

(21) Appl. No.: 18/028,775

(22) PCT Filed: Nov. 6, 2020

(86) PCT No.: PCT/JP2020/041527
§ 371 (c)(1),
(2) Date: Mar. 28, 2023

(87) PCT Pub. No.: WO2022/097273
PCT Pub. Date: May 12, 2022

(65) Prior Publication Data
US 2023/0329610 A1      Oct. 19, 2023

(51) Int. Cl.
*A61B 5/16*          (2006.01)
*G06F 13/00*         (2006.01)
*H04L 12/12*         (2006.01)
(52) U.S. Cl.
CPC .............. *A61B 5/167* (2013.01); *G06F 13/00* (2013.01); *H04L 12/12* (2013.01)

(58) Field of Classification Search
CPC .......... A61B 5/167; H04L 12/12; G06F 13/00
See application file for complete search history.

(56) References Cited

U.S. PATENT DOCUMENTS 11,637,738 B2 *   4/2023   Defiebre ............. G06F 21/6245
                                                          709/202
2005/0257006 A1   11/2005   Yoshida et al.
2006/0053219 A1    3/2006   Kutsumi et al.
(Continued)

FOREIGN PATENT DOCUMENTS

EP          3217349 A1      9/2017
GB          2446618 A   *  8/2008   ....... G06F 17/30035
(Continued)

OTHER PUBLICATIONS

International Search Report and Written Opinion mailed on Feb. 2, 2021, received for PCT Application PCT/JP2020/041527, filed on Nov. 6, 2020, 8 pages including English Translation.
(Continued)

*Primary Examiner* — Sumaiya A Chowdhury
(74) *Attorney, Agent, or Firm* — XSENSUS LLP

(57)                ABSTRACT

A device control apparatus (110) includes a personality-information acquiring unit (114) that acquires personality information indicating a personality of a user, a control-method specifying unit (115) that specifies a device control method that is a control method for a device (101) used by the user from the personality information and a lifestyle pattern of the user, and a control unit (116) that controls the device (101) in accordance with the device control method.

18 Claims, 9 Drawing Sheets

(56) References Cited

U.S. PATENT DOCUMENTS

| | | | |
|---|---|---|---|
| 2018/0139067 A1* | 5/2018 | Josyula | H04L 67/306 |
| 2020/0244768 A1 | 7/2020 | Gibson et al. | |
| 2023/0211744 A1* | 7/2023 | Giersch | B60W 50/085 |
| | | | 701/36 |

FOREIGN PATENT DOCUMENTS

| | | |
|---|---|---|
| JP | 2003-111157 A | 4/2003 |
| JP | 2004-185612 A | 7/2004 |
| JP | 3744932 B2 | 2/2006 |
| JP | 2008-058193 A | 3/2008 |
| JP | 2018-083269 A | 5/2018 |
| JP | 2018-120506 A | 8/2018 |
| WO | 2008/103546 A1 | 8/2008 |

OTHER PUBLICATIONS

John et al., "Paradigm Shift to the Integrative Big Five Trait Taxonomy", Handbook of personality: Theory and research, vol. 3, No. 2, 2008, pp. 114-158.

Tangney et al., "High Self-control Predicts Good Adjustment, Less Pathology, Better Grades, and Interpersonal Success", Journal of Personality, vol. 72, No. 2, Apr. 2004, pp. 271-324.

Youyou et al., "Computer-based personality judgments are more accurate than those made by humans", Proceedings of the National Academy of Sciences, vol. 112, No. 4, Jan. 27, 2015, pp. 1036-1040.

Stachl et al., "Predicting personality from patterns of behavior collected with smartphones", Proceedings of the National Academy of Sciences, vol. 117, No. 30, Jul. 28, 2020, pp. 17680-17687.

Extended European Search Report issued Jul. 31, 2023 in corresponding European Patent Application No. 20960825.6, 17 pages.

Bourobou Serge et. Al., "User Activity Recognition in Smart Homes Using Pattern Clustering Applied to Temporal ANN Algorithm", Sensors, vol. 15, No. 5, May 21, 2015, pp. 11953-11971, XP093064972, DOI: 10.3390/s150511953.

Office Action issued Feb. 26, 2025 in European Patent Application No. 20 960 825.6, 15 pages.

Office Action issued May 16, 2025 in Chinese Patent Application No. 202080106692.1, 25 pages.

* cited by examiner

| | 120a | 120b | 120c | |
|---|---|---|---|---|
| | EVENT TIME AND DATE | TYPE | EVENT CONTENT | ... |
| | 2020/07/01 06:07 | HUMAN DETECTION SENSOR | DETECTION | ... |
| | 2020/07/01 06:08 | AIR CONDITIONER | COOLING ON | ... |
| | 2020/07/01 06:29 | TELEVISION | VIEWING ON | ... |
| | ⋮ | ⋮ | ⋮ | ⋮ |
| | 2020/07/01 07:30 | TELEVISION | VIEWING OFF | ... |
| | 2020/07/01 07:31 | AIR CONDITIONER | COOLING OFF | ... |
| | ⋮ | ⋮ | ⋮ | ⋮ |
| | 2020/07/31 05:58 | AIR CONDITIONER | COOLING ON | ... |
| | 2020/07/31 06:28 | TELEVISION | VIEWING ON | ... |
| | ⋮ | ⋮ | ⋮ | ⋮ |

*FIG. 4A*
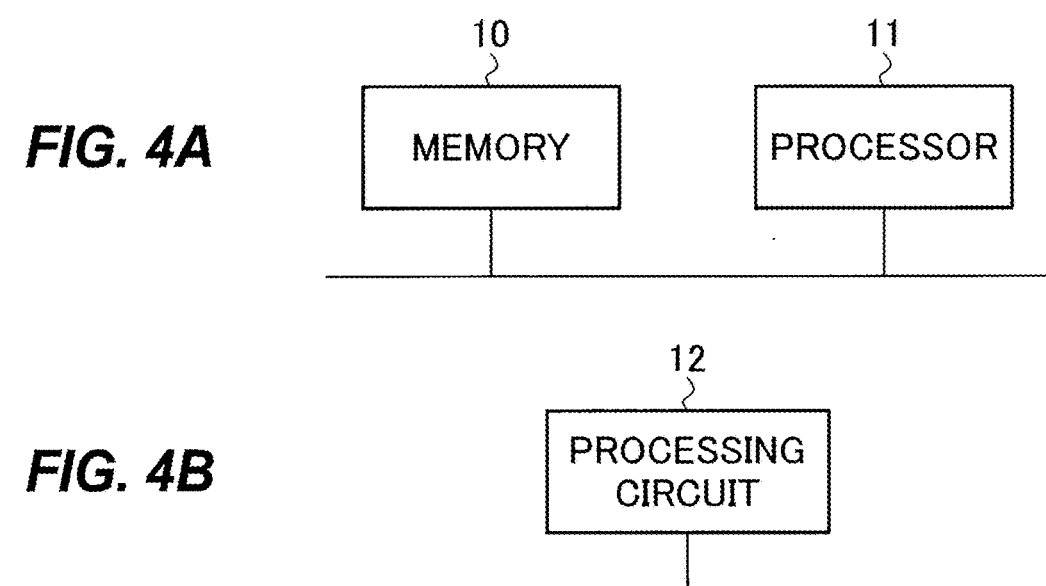
*FIG. 4B*
*FIG. 5*
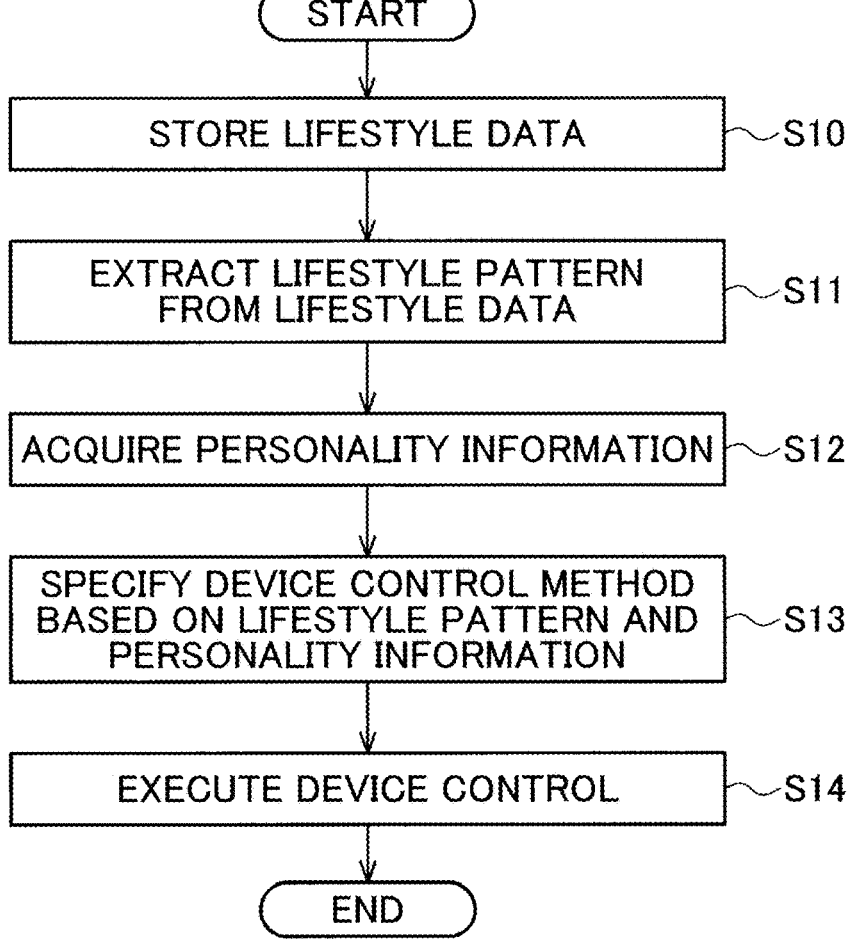

FIG. 12

| | | MANIPULATION LINKED TO TRIGGER | | | |
|---|---|---|---|---|---|
| | | TURN ON AIR CONDITIONER COOLING | TURN OFF AIR CONDITIONER COOLING | TURN ON TELEVISION VIEWING | TURN OFF TELEVISION VIEWING |
| TRIGGERING MANIPULATION OR OPERATION | TURN ON AIR CONDITIONER COOLING | — | — | 89% | 6% |
| | TURN OFF AIR CONDITIONER COOLING | — | — | 3% | 58% |
| | TURN ON TELEVISION VIEWING | 92% | 4% | — | — |
| | TURN OFF TELEVISION VIEWING | 5% | 76% | — | — |
| | DETECTION BY HUMAN DETECTION SENSOR | 65% | 3% | 45% | 4% |

FIG. 13

| | | MANIPULATION LINKED TO TRIGGER | | | |
|---|---|---|---|---|---|
| | | TURN ON AIR CONDITIONER COOLING | TURN OFF AIR CONDITIONER COOLING | TURN ON TELEVISION VIEWING | TURN OFF TELEVISION VIEWING |
| TRIGGERING MANIPULATION OR OPERATION | TURN ON AIR CONDITIONER COOLING | — | — | 89% | 6% |
| | TURN OFF AIR CONDITIONER COOLING | — | — | 3% | 58% |
| | TURN ON TELEVISION VIEWING | 92% | 4% | — | — |
| | TURN OFF TELEVISION VIEWING | 5% | 76% | — | — |
| | DETECTION BY HUMAN DETECTION SENSOR | 65% | 3% | 45% | 4% |

FIG. 14

| | | MANIPULATION LINKED TO TRIGGER | | | |
|---|---|---|---|---|---|
| | | TURN ON AIR CONDITIONER COOLING | TURN OFF AIR CONDITIONER COOLING | TURN ON TELEVISION VIEWING | TURN OFF TELEVISION VIEWING |
| TRIGGERING MANIPULATION OR OPERATION | TURN ON AIR CONDITIONER COOLING | — | — | 89% | 6% |
| | TURN OFF AIR CONDITIONER COOLING | — | — | 3% | 58% |
| | TURN ON TELEVISION VIEWING | 92% | 4% | — | — |
| | TURN OFF TELEVISION VIEWING | 5% | 76% | — | — |
| | DETECTION BY HUMAN DETECTION SENSOR | 65% | 3% | 45% | 4% |

FIG. 15

| | | MANIPULATION LINKED TO TRIGGER | | | |
|---|---|---|---|---|---|
| | | TURN ON AIR CONDITIONER COOLING | TURN OFF AIR CONDITIONER COOLING | TURN ON TELEVISION VIEWING | TURN OFF TELEVISION VIEWING |
| TRIGGERING MANIPULATION OR OPERATION | TURN ON AIR CONDITIONER COOLING | — | — | 89% | 6% |
| | TURN OFF AIR CONDITIONER COOLING | — | — | 3% | 58% |
| | TURN ON TELEVISION VIEWING | 92% | 4% | — | — |
| | TURN OFF TELEVISION VIEWING | 5% | 76% | — | — |
| | DETECTION BY HUMAN DETECTION SENSOR | 65% | 3% | 45% | 4% |

FIG. 16

| | | MANIPULATION LINKED TO TRIGGER | | | |
|---|---|---|---|---|---|
| | | TURN ON AIR CONDITIONER COOLING | TURN OFF AIR CONDITIONER COOLING | TURN ON TELEVISION VIEWING | TURN OFF TELEVISION VIEWING |
| TRIGGERING MANIPULATION OR OPERATION | TURN ON AIR CONDITIONER COOLING | — | — | 89% | 6% |
| | TURN OFF AIR CONDITIONER COOLING | — | — | 3% | 58% |
| | TURN ON TELEVISION VIEWING | 92% | 4% | — | — |
| | TURN OFF TELEVISION VIEWING | 5% | 76% | — | — |
| | DETECTION BY HUMAN DETECTION SENSOR | 65% | 3% | 45% | 4% |

DEVICE CONTROL APPARATUS, NON-TRANSITORY COMPUTER-READABLE MEDIUM, AND DEVICE CONTROL METHOD

CROSS-REFERENCE TO RELATED APPLICATION

The present application is based on PCT filing PCT/JP2020/041527, filed Nov. 6, 2020, the entire contents of which are incorporated herein by reference.

TECHNICAL FIELD

The disclosure relates to a device control apparatus, non-transitory computer-readable medium, and a device control method.

BACKGROUND ART

Conventionally, characteristic lifestyle patterns of a user are extracted from the user's usage history of devices, and these lifestyle patterns are used to control the devices in accordance with the user's lifestyle pattern and situation. For example, Patent Literature 1 discloses a technique of using content related to specific episodes in lifestyle data as element data items and combining these element data items to create episode data, a technique of analyzing the relationship between the element data items in the episode data, a technique of specifying lifestyle patterns characteristic to a user from the relationship between the element data items, and a technique of controlling devices by using lifestyle pattern information of the user.

PRIOR ART REFERENCE

Patent Reference

Patent Literature 1: Japanese Patent No. 3744932

SUMMARY OF THE INVENTION

Problem to be Solved by the Invention

However, whether or not device control using lifestyle patterns is desirable for users depends on the users' unique personalities. Therefore, if the control content is determined solely by lifestyle patterns, certain users feel that such control content is undesirable. As a result, there is an issue that after such experience, certain users discontinue the use of device control services or will be less satisfied with the device control service.

Accordingly, it is an object of one or more aspects of the disclosure to enables execution of device control in accordance with a user's lifestyle pattern and a user's personality.

Means of Solving the Problem

A device control apparatus according to an aspect of the disclosure includes a personality-information acquiring unit that acquires personality information indicating a personality of a user, a control-method specifying unit that specifies a device control method that is a control method for a device used by the user from the personality information and a lifestyle pattern of the user, and a control unit that controls the device in accordance with the device control method.

A program according to an aspect of the disclosure causes a computer to function as a personality-information acquiring unit that acquires personality information indicating a personality of a user, a control-method specifying unit that specifies a device control method that is a control method for a device used by the user from the personality information and a lifestyle pattern of the user, and a control unit that controls the device in accordance with the device control method.

A device control method according to an aspect of the disclosure includes acquiring personality information indicating a personality of a user, specifying a device control method that is a control method for a device used by the user from the personality information and a lifestyle pattern of the user, and controlling the device in accordance with the device control method.

Effects of the Invention

According to one or more aspects of the disclosure, it is possible to execute device control in accordance with a user's lifestyle pattern and a user's personality.

BRIEF DESCRIPTION OF THE DRAWINGS

FIG. 1 is a block diagram schematically illustrating a configuration of a device control system including a device control apparatus according to first and second embodiments.

FIGS. 4A and 4B are block diagrams illustrating hardware configuration examples.

FIG. 5 is a flowchart illustrating an example of the overall operation of a device control apparatus.

FIG. 12 is a table indicating an example lifestyle pattern according to the second embodiment.

FIG. 13 is a table explaining a first example of specifying a device control method on the basis of a frequency of an operation of a linked device.

FIG. 14 is a table explaining a second example of specifying a device control method on the basis of a frequency of an operation of a linked device.

FIG. 15 is a table explaining a third example of specifying a device control method on the basis of a frequency of an operation of a linked device.

FIG. 16 is a table explaining a fourth example of specifying a device control method on the basis of a frequency of an operation of a linked device.

MODE FOR CARRYING OUT THE INVENTION

First Embodiment

Figure 1:
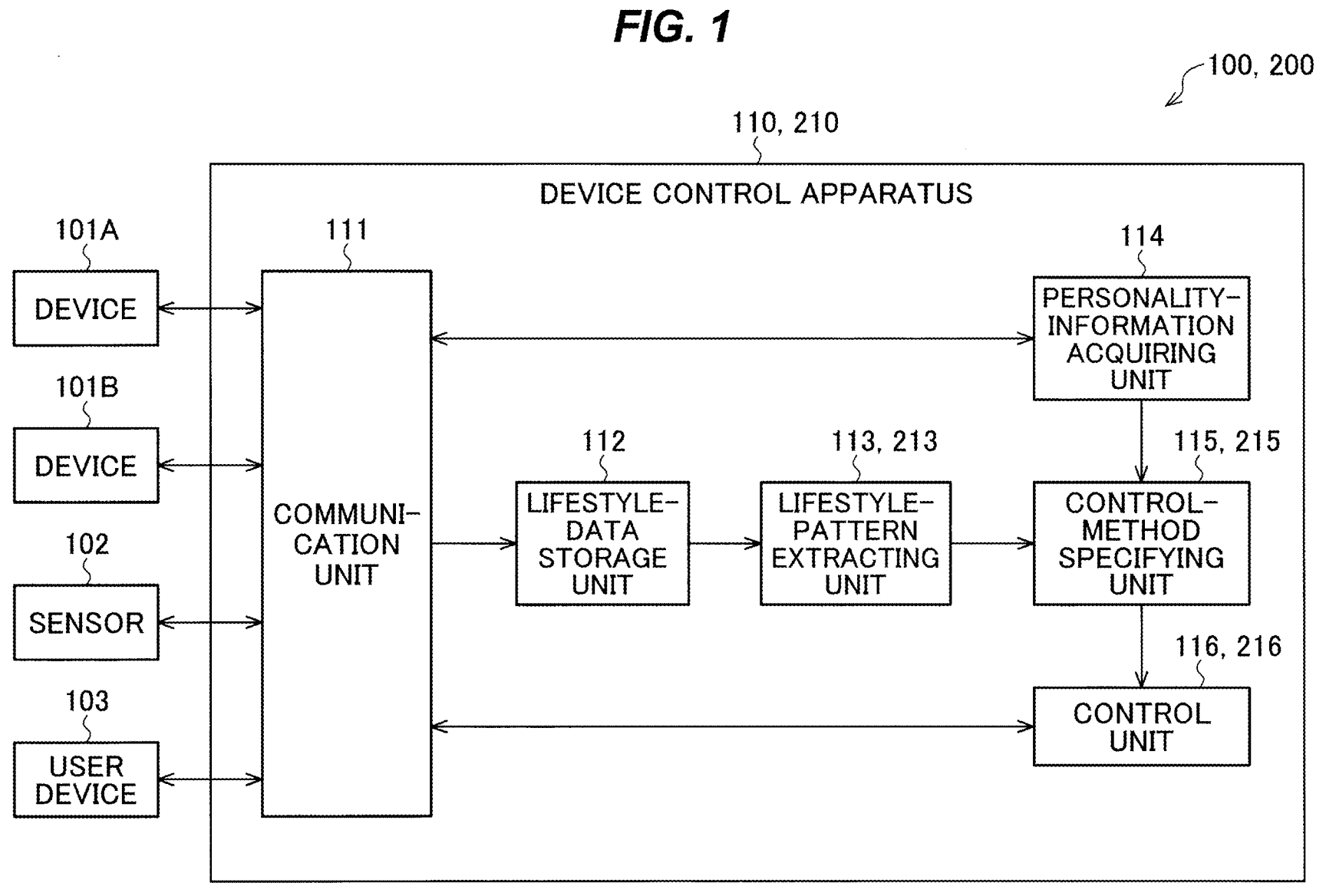
Figures 2, 3:
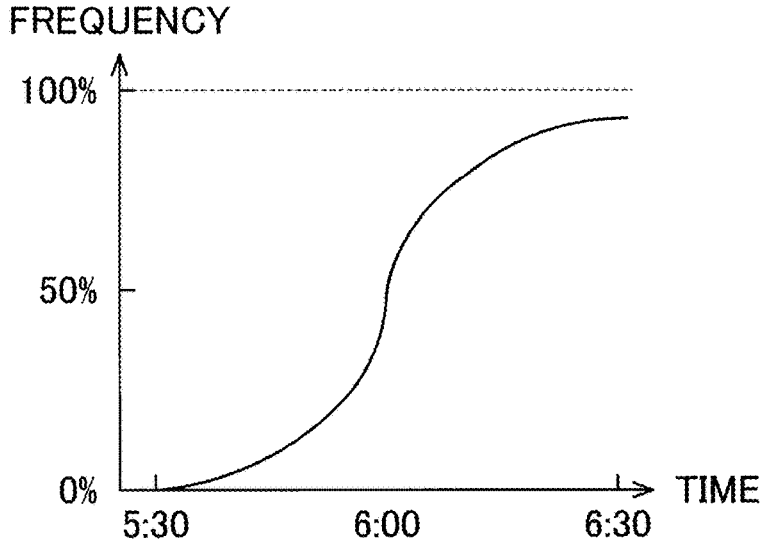
FIG. 2 is a schematic diagram illustrating an example of lifestyle data.
FIG. 3 is a schematic diagram illustrating an example lifestyle pattern according to the first embodiment.

FIG. 1 is a block diagram schematically illustrating a configuration of a device control system 100 including a device control apparatus 110 according to the first embodiment.

The device control system 100 includes devices 101A and 101B, a sensor 102, a user device 103, and a device control apparatus 110.

The devices 101A and 101B are targets to be controlled by the device control apparatus 110. The devices 101A and 101B may be devices such as air conditioners, refrigerators, cooking heaters, ranges, EcoCute machines, or lighting fixtures.

Note that when there is no need to distinguish between the devices 101A and 101B, the devices 101A and 101B are referred to as devices 101. The device control system 100 may include one device 101 or two or more devices 101.

The sensor 102 is a sensor that detects a predetermined target, such as a human detection sensor, an opening/closing sensor, a thermo-hygrometer, a photometer, a carbon dioxide concentration meter, a pressure sensor, or an acceleration sensor.

The sensor 102 may be installed inside any of the devices 101. The device control system 100 may include one or more sensors 102 or no sensor 102.

The user device 103, which is a device such as a smartphone or a smart speaker, transmits information to a user using a control target device 101 and accepts input from the user.

The device 101, such as a television or a refrigerator, may also serve as the user device 103. When there are multiple users using the control target device 101, multiple user devices 103 may exist, and each user may have a user device 103.

The device control apparatus 110 controls the devices 101.

As illustrated in FIG. 1, the device control apparatus 110 includes a communication unit 111, a lifestyle-data storage unit 112, a lifestyle-pattern extracting unit 113, a personality-information acquiring unit 114, a control-method specifying unit 115, and a control unit 116.

The communication unit 111 is an interface that communicates with the devices 101, the sensor 102, and the user device 103.

The lifestyle-data storage unit 112 stores lifestyle data.

The lifestyle data indicates at least a history of multiple events related to the devices 101. The lifestyle data may contain a history of multiple events related to the sensor 102.

A history of multiple events is, for example, a manipulation history or an operation history of the devices 101 or the sensor 102. Manipulation refers to, for example, an on-manipulation, an off-manipulation, a setting change manipulation, a timer setting manipulation, or the like. Operation refers to, for example, start of operation, completion of operation, change of operation, detection by the sensor 102, periodic acquisition of measurement values by the sensor 102, or the like.

FIG. 2 is a schematic diagram illustrating an example of lifestyle data.

As illustrated in FIG. 2, lifestyle data 120 is table information having an event date-and-time column 120a, a type column 120b, and an event content column 120c.

The event date-and-time column 120a stores the date and time of events.

The type column 120b stores the type of device 101 or sensor 102 subjected to an event.

The event content column 120c stores information indicating the content of events. The event content column 120c may store, for example, detection by the sensor 102, use (for example, an on-manipulation) or termination (for example, an off-manipulation) of a function of a device 101, and the like. If a device 101 has only one function, the use or termination of the device 101 may indicate the use or termination of this function.

The lifestyle data 120 may also contain identification or the like that is identification information for identifying the devices 101 and the sensor 102.

In the example of FIG. 2, the device 101A is an air conditioner, the device 101B is a television, and the sensor 102 is a human detection sensor; however, the devices 101 and the sensor 102, which are connected to the device control apparatus 110 and store histories, are not limited to these.

As illustrated in FIG. 2, the event content related to the devices 101 is not limited to on and off manipulations. For example, for an air conditioner, the event content may be a manipulation of changing a set temperature or a temperature measured by a thermometer built in the air conditioner exceeding a preset threshold.

Referring back to FIG. 1, the lifestyle-pattern extracting unit 113 extracts lifestyle patterns from the lifestyle data stored in the lifestyle-data storage unit 112.

A lifestyle pattern according to the first embodiment is the frequency of a function of a device 101 being used under each condition such as time.

For example, the lifestyle data contains multiple manipulations performed on a function of a device 101 as events related to the device 101. The lifestyle-pattern extracting unit 113 refers to the lifestyle data to calculate the frequency of each of the manipulations being performed within each predetermined time zone and to extract the frequency of each of the manipulations within each predetermined time zone as the lifestyle pattern.

FIG. 3 is a graph indicating an example of a lifestyle pattern according to the first embodiment.

FIG. 3 is a graph indicating the frequency of air-conditioner cooling being turned on at each time.

The lifestyle pattern according to the first embodiment is the frequency in each predetermined time zone and is determined by dividing the number of times a specific function (cooling, in this case) is used in each time zone within a specific period divided by the number of days in that specific period.

The specific period is, for example, a predetermined period from the day on which the lifestyle pattern was extracted, e.g., the past month. The specific period may be changed as needed.

The lifestyle-pattern extracting unit 113 may divide the specific period into weekdays and holidays and calculate the frequency in each time zone on weekdays and holidays to determine a lifestyle pattern. This is preferred because it allows device control tailored to lifestyle patterns of both weekdays and holidays.

Besides the frequency in each time zone, the lifestyle pattern may be, for example, the frequency of a function being used at each room temperature.

It suffices to preset a time zone, for example, to 30 minutes so that it is shorter than the specific period described above.

Referring back to FIG. 1, the personality-information acquiring unit 114 acquires personality information indicating the personality of a user using a device 101.

The personality information is, for example, the Big Five personality traits. The Big Five personality traits, also known as the five-factor model, characterize personality by five parameters: openness, diligence, extraversion, agreeableness, and emotional stability. That is, personality information may contain such parameters as elements. The Big Five personality traits are described in detail in the following literature.

John, Oliver P., Laura P. Naumann, and Christopher J. Soto. "Paradigm shift to the integrative big five trait taxonomy." Handbook of personality: Theory and research 3.2 (2008), pp. 114-158.

Openness represents the degree of preferring new experiences or diversity and may be rephrased as openness to experience.

Diligence represents the tendency to be ambitious and achievement-oriented or to prefer deliberate behavior and may be rephrased as conscientiousness.

Extraversion represents the degree of preferring socializing or talking with others.

Agreeableness represents the tendency to be cooperative with others and may be rephrased as harmonization or attachment.

Emotional stability represents the tendency to have a stable personality and be less likely to experience unpleasant emotions and may be rephrased as neuroticism in the opposite sense.

Personality information may contain, for example, a parameter indicating the strength of self-control as an element. Self-control is described in detail in the following literature.

Tangney, June P., Roy F. Baumeister, and Angie Luzio Boone. "High self-control predicts good adjustment, less pathology, better grades, and interpersonal success." Journal of Personality 72.2 (2004), pp. 271-324.

Self-control is the self-motivated pursuit of desirable behaviors and the suppression of undesirable behaviors in the face of temptation or impulse.

Personality information may contain other parameters for which definitions and measurement methods are established in the field of psychology. When there are multiple users using a device 101, it is preferred to provide such personality information for each user.

The personality-information acquiring unit 114 then may acquire personality information, for example, by conducting a questionnaire on about users their personality. The questionnaire may be conducted by using the user device 103 or face-to-face at the time of purchase of the device 101. The personality-information acquiring unit 114 may acquire score values of an already measured personality scale through a network or the like or by input by the users.

Personality information may be, for example, inferred from a manipulation history such as clicking a "Like!" button on a social network service (SNS) or a writing history and be acquired via a network or the like. Such a method of acquisition is described in detail in the following literature.

Youyou, Wu, Michal Kosinski, and David Stillwell. "Computer-based personality judgments are more accurate than those made by humans." Proceedings of the National Academy of Sciences 112.4 (2015), pp. 1036-1040.

Furthermore, personality information may be inferred from manipulation history, operation history, or the contents stored in a user device, such as a smartphone, and be acquired via a network or the like. Such a method of inference is described in detail in the following literature.

Stachl, Clemens, et al. "Predicting personality from patterns of behavior collected with smartphones." Proceedings of the National Academy of Sciences 117. 30 (2020), pp. 17680-17687.

The user device used to acquire personality information may be the same as or different from the user device 103 illustrated in FIG. 1.

When multiple users use a device 101, and personality information of f these users is to be acquired, the personality information may be acquired by repeating the aforementioned method of acquisition by questionnaire or inference for the number of users.

For each control target device 101, it is preferred to register the users of the device 101 so that the device 101 can be controlled in accordance with the personality of the user who is using the device 101. In such a case, it is preferred to set the frequency or time zone of use for each user in order to improve precision specific to the user and thereby enable the device 101 to be controlled in accordance with the user's personality.

Furthermore, it is preferred to preset a sensor or the like so that the user can be identified. The sensor for identifying an individual may be the same as or different from the sensor 102 illustrated in FIG. 1. For example, in the case where the sensor is a camera built into the device 101, the user's facial image is registered in advance to enable identification of the individual using the device 101.

In the case where the sensor 102 is a fingerprint sensor attached to a manipulation button of a device 101, the user may be identified by the fingerprint sensor. In the case where the user manipulates the device 101 by voice, the user may be identified by voice information. In the case where the user manipulates the device 101 via a user device held by each user, the user may be identified by registration information of the user device used for the manipulation.

The control-method specifying unit 115 specifies a device control method that is a control method of the device 101 on the basis of the lifestyle patterns extracted by the lifestyle-pattern extracting unit 113 and the personality information acquired by the personality-information acquiring unit 114.

For example, the control-method specifying unit 115 specifies a threshold on the basis of personality information and compares the specified threshold with the lifestyle patterns to specify a control method of the device 101.

Specifically, the control-method specifying unit 115 refers to the personality information to specify a threshold in accordance with the personality of the user and to specify a device control method when the frequency indicated by the lifestyle pattern exceeds the threshold so that the device control method causes control related to a corresponding manipulation to be executed within a corresponding time zone.

In the first embodiment, the control-method specifying unit 115 specifies, as a device control method, a first device control method for automatically performing a corresponding manipulation as control when a first threshold serving as a threshold is exceeded and specifies a second device control method for recommending the corresponding manipulation to be performed as control when a second threshold serving as a threshold lower than the first threshold is exceeded. Details of the method for specifying a device control method will be described in detail later.

The control controls a device 101 in accordance with a device control method specified by the control-method specifying unit 115.

A portion or the entirety of the lifestyle-pattern extracting unit 113, the personality-information acquiring unit 114, the control-method specifying unit 115, and the control unit 116 described above can be implemented by, for example, a memory 10 and a processor 11, such as a central processing unit (CPU), that executes the programs stored in the memory 10, as illustrated in FIG. 4A. Such programs may be provided via a network or may be recorded and provided on a recording medium. That is, such programs may be provided as, for example, program products. As described above, the device control apparatus 110 can be implemented by a computer.

A portion or the entirety of the lifestyle-pattern extracting unit 113, the personality-information acquiring unit 114, the control-method specifying unit 115, and the control unit 116 can be implemented by, for example, a processing circuit 12, such as a single circuit, a composite circuit, a processor running on a program, a parallel processor running on a program, an application-specific integrated circuit (ASIC), or a field programmable gate array (FPGA), as illustrated in FIG. 4B.

As described above, the lifestyle-pattern extracting unit 113, the personality-information acquiring unit 114, the control-method specifying unit 115, and the control unit 116 can be implemented by processing circuitry.

Note that the lifestyle-data storage unit 112 can be implemented by a storage medium, which is, for example, such as a memory such as a read-only memory (ROM) or a random-access memory or a storage medium such as a hard disc drive (HDD) or a solid-state drive (SDD).

The communication unit 111 can be implemented by a communication device such as a network interface card (NIC).

The lifestyle-data storage unit 112, the lifestyle-pattern extracting unit 113, the personality-information acquiring unit 114, the control-method specifying unit 115, or the control unit 116 may exist on a cloud server, be a separate device, or be built into either a device 101 or the sensor 102. These configurations may be divided into several sections and exist separately in the form described above.

The operation of the device control apparatus 110 will now be explained.

FIG. 5 is a flowchart illustrating an example of the overall operation of the device control apparatus 110.

First, the communication unit 111 receives lifestyle data from a device 101, the sensor 102, or the like and stores the lifestyle data in the lifestyle-data storage unit 112 (step S10).

The lifestyle-pattern extracting unit 113 extracts a lifestyle pattern from the stored lifestyle data (step S11).

The personality-information acquiring unit 114 acquires personality information of a user via the communication unit 111 (step S12).

The control-method specifying unit 115 specifies a device control method that is a control method of the device 101 on the basis of the lifestyle pattern and the personality information (step S13).

The control unit 116 controls the device 101 on the basis of the device control method specified by the control-method specifying unit 115 (step S14).

The device control method specified in step S13 in FIG. 5 will now be explained.

In the first embodiment, automatic control and recommendation are performed as a device control method.

Automatic control is a device control method that automatically performs a manipulation that is highly frequent in the lifestyle pattern and highly likely to be performed by the user. The device control method for executing automatic control is also referred to as a first device control method.

Recommendation is a device control method that notifies the user in advance that a manipulation frequent in the lifestyle pattern and likely to be performed by the user is to be performed and the corresponding control is to be executed if the user accepts the notification. The device control method for making a recommendation is also referred to as a second device control method.

Figure 6:
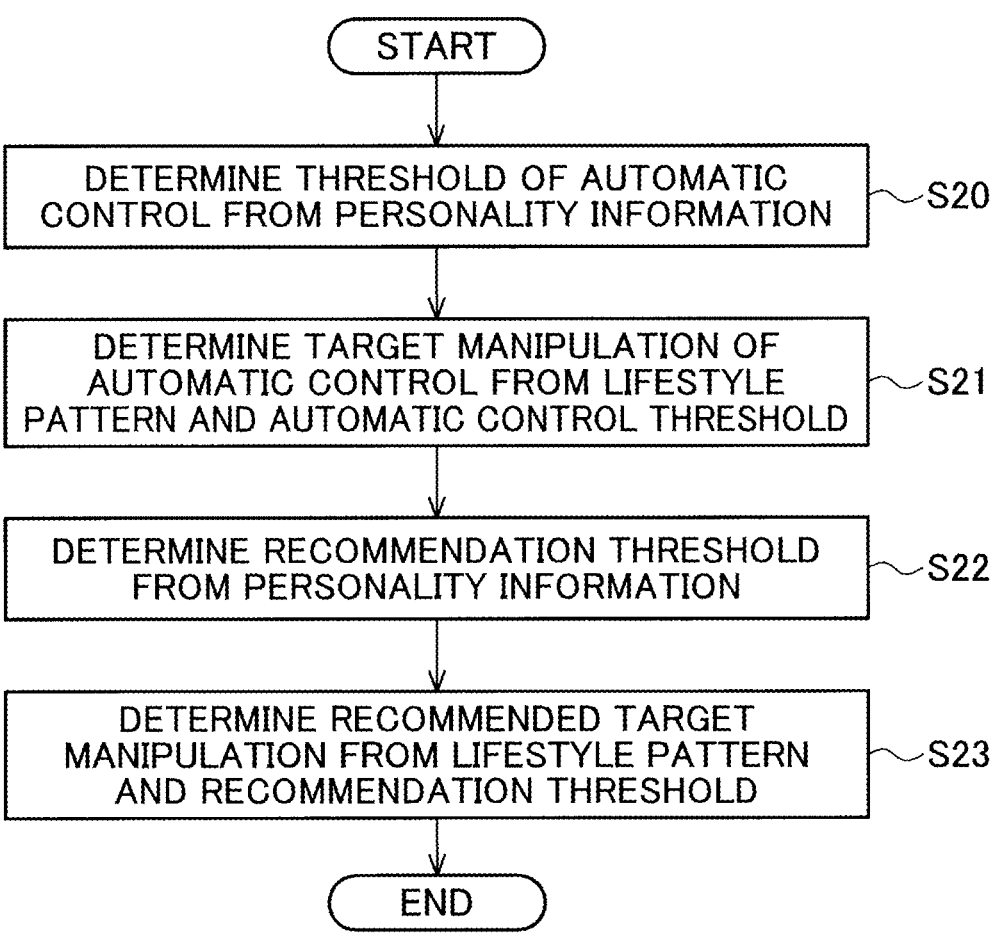
FIG. 6 is a flowchart illustrating an operation of a control-method specifying unit.

FIG. 6 is a flowchart illustrating the operation of the control-method specifying unit 115.

The control-method specifying unit 115 determines an automatic control threshold that is a threshold of automatic control in accordance with the personality information acquired by the personality-information acquiring unit 114 (step S20). The automatic control threshold is also referred to as a first threshold.

The control-method specifying unit 115 determines a target manipulation to be performed under automatic control and the time of performing the manipulation on the basis of the lifestyle pattern extracted by the lifestyle-pattern extracting unit 113 and the automatic control threshold determined in step S20 (step S21). Here, the time may be any time within a corresponding time zone. For example, the time may be a start time, which is the time at which the time zone starts; an intermediate time that is in the middle of the time zone; or an end time that is the time at which the time zone ends. The time may also be an average time, that is the average time at which the event used to calculate the threshold took place.

The control-method specifying unit 115 determines a recommendation threshold, which is a threshold of recommendation, in accordance with the personality information acquired by the personality-information acquiring unit 114 (step S22). The recommendation threshold is also referred to as a second threshold.

The control-method specifying unit 115 determines a target manipulation to be recommended and a time of recommendation on the basis of the lifestyle pattern extracted by the lifestyle-pattern extracting unit 113 and the recommendation threshold determined in step S22 (step S23). Here, the time may be any time within a corresponding time zone. For example, the time may be a start time, which is the time at which the time zone starts; an intermediate time that is in the milled of the time zone; or an end time that is the time at which the time zone ends. The time may also be an average time, that is the average time at which the event used to calculate the threshold took place.

Here, the determination of the threshold in steps S20 to S23 in FIG. 6 and the determination of the target manipulation to be controlled and the time will now be described in detail.

Figure 7:
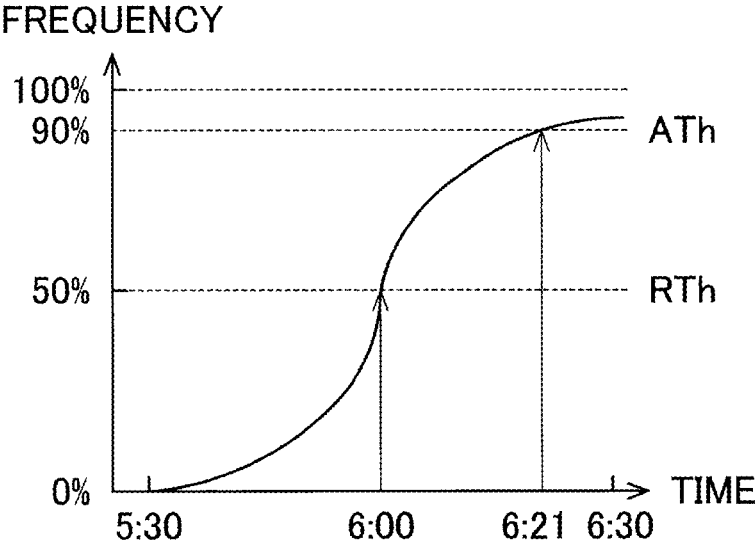
FIG. 7 is a graph plaining a first example of specifying a device control method.

FIG. 7 is a graph explaining a first example of specifying a device control method.

FIG. 7 explains an example in which the device 101 is an air conditioner, and a control method is specified on the basis of the frequency of cooling being turned on. Here, the personality information of the user is presumed to be average. This is a case in which, for example, all parameters in the personality information indicating openness, diligence, extraversion, agreeableness, emotional stability, and self-control are within a predetermined numerical range. The numerical range here may be the same for all parameters or different for each parameter.

In such a case, the control-method specifying unit 115 determines, for example, an automatic control threshold ATh for turning on cooling by the device 101 from an off state to be an automatic control reference threshold 90%, which is a reference threshold for automatic control, and a recommendation threshold RTh for turning on cooling by the device 101 from an off state to be a recommendation reference threshold 50%, which is a reference threshold for recommendation.

The control-method specifying unit 115 then executes automatic control to turn on cooling by an air conditioner or the device 101 when the frequency of the air conditioner cooling being turned on exceeds the automatic control threshold ATh, and the time of the automatic control is the time when the frequency exceeds the automatic control threshold ATh.

The control-method specifying unit 115 recommends turning on air conditioner cooling when the frequency of the air conditioner cooling being turned on exceeds the recommendation threshold RTh, and the time of recommendation is the time when the frequency exceeds the recommendation threshold RTh.

In the example of FIG. 7, the control-method specifying unit 115 specifies a device control method that recommends turning on the air conditioner cooling at 6:00 and executes automatic control to turn on the air conditioner cooling at 6:21.

When the frequency of a function of the device 101 being turned on fluctuates up and down across a threshold, the control-method specifying unit 115 may apply a rule to the device control method so that control is not unnecessarily executed. For example, the device control method may adopt a rule of not executing automatic control related to the same manipulation for 30 minutes after the time at which automatic control has been executed or a rule of not making recommendations related to the same manipulation for 30 minutes after the time at which a recommendation has been made.

The control-method specifying unit 115 may execute control to turn off a function of the device 101 from an on state on the basis of the frequency of the function of the device 101 being turned on.

The control-method specifying unit 115 may determine, for example, an automatic control threshold for the control of turning off the function of the device 101 from an on state to be an automatic control reference threshold 10% and a recommendation threshold to be a recommendation reference threshold 50%.

In the example of FIG. 7, a device control method is specified on the basis of the frequency of the air conditioner cooling being turned on, but similarly, the device control method may be specified on the basis of the frequency of a function of a device 101 other than the air conditioner, the frequency of a certain function that is not turned on being used, the frequency of a value measured by the sensor 102 exceeding a threshold, and the like.

A case will now be described in which the control-method specifying unit 115 specifies a threshold in accordance with personality information of a user to cause device control to occur easily.

Figure 8:
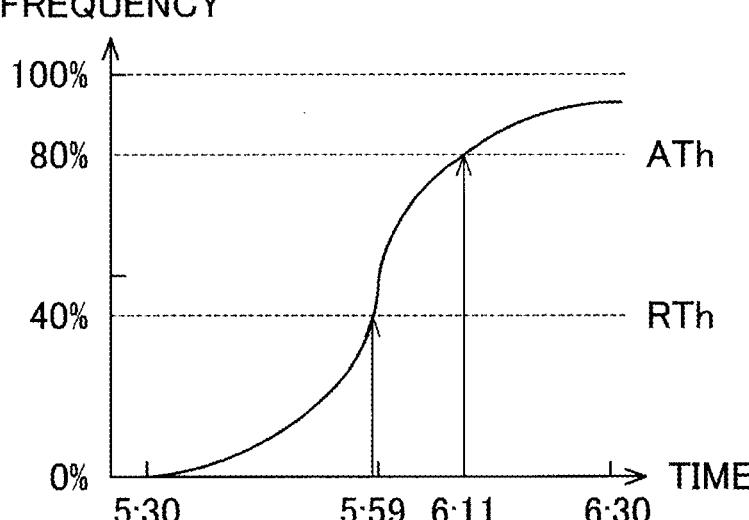
FIG. 8 is a graph explaining a second example of specifying a device control method.

FIG. 8 is a graph explaining a second example of specifying a device control method.

On the basis of personality information of a user, if causing device control to occur easily improves the effect of the service provided by the device control, e.g., if the user has high openness, high emotional stability, low diligence, or low self-control, the control-method specifying unit 115 causes the device control to occur easily by lowering the control threshold.

This is a case in which, for example, on the basis of personality information, openness is higher than a predetermined numerical range, emotional stability is higher than a predetermined numerical range, diligence is lower than a predetermined numerical range, or self-control is lower than a predetermined numerical range.

In such a case, the control-method specifying unit 115 specifies, for example, the automatic control threshold ATh to be 80%, which is lower than the automatic control reference threshold, and the recommendation threshold RTh to be 40%, which is lower than the recommendation reference threshold. At this time, the control-method specifying unit 115 specifies a device control method that recommends turning on air conditioner cooling at 5:59 and executes automatic control to turn on air conditioner cooling at 6:11. In this way, the control time is moved up further than that in the case of FIG. 7 in which the personality information is average. Moreover, lowering of the threshold results in an increase in the frequency of device control.

For example, if openness is high in the personality information of the user, there is a high tendency of the user to favor automatic control or a recommendation by the device control apparatus 110 because the user perceives the automatic control or recommendation as a new experience or a variation in lifestyle. For example, if emotional stability is high in the personality information of the user, there is a small possibility that the user feels unpleasant about control by the device control apparatus 110. Therefore, device control can be executed earlier or more frequently, as described above, to enhance the effect of the service by device control without causing discomfort to the user.

For example, if diligence or self-control is low in the personality information of the user, there is much room for transforming the user's behavior into a desired behavior by supporting planned behavior of the user by the device control apparatus 110. Therefore, by performing device control earlier or increasing the frequency as described above, the user can be supported more strongly, and the effect of service by device control can be improved.

A case will now be described in which the control-method specifying unit 115 specifies a threshold in accordance with personality information user, to cause device control not to occur easily.

Figure 9:
FIG. 9 is a graph explaining a third example of specifying a device control method.
Figure 9:
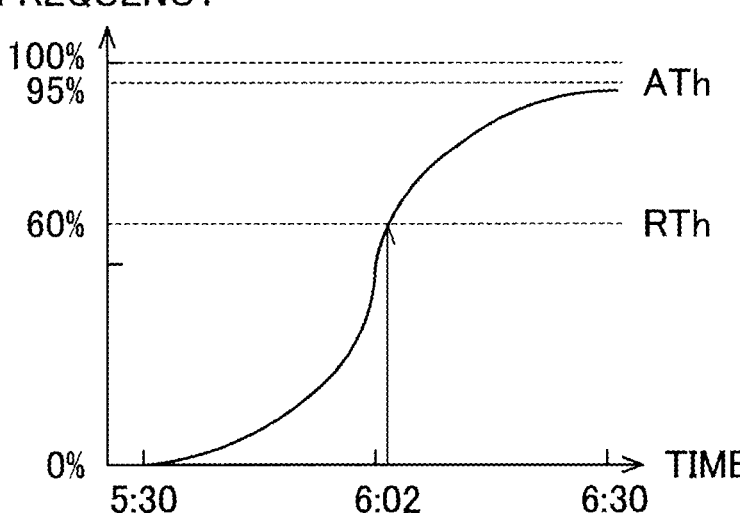

FIG. 9 is a graph explaining a third example of specifying a device control method.

On the basis of personality information of a user, if causing device control not to occur easily improves the effect of a service provided by the device control, e.g., if the user has low openness, low emotional stability, high diligence, or high self-control, the control-method specifying unit 115 causes the device control not to occur easily by raising the control threshold.

This is a case in which, for example, on the basis of personality information, openness is lower than a predetermined numerical range, emotional stability is lower than a predetermined numerical range, diligence is higher than a predetermined numerical range, or self-control is higher than a predetermined numerical range.

In such a case, the control-method specifying unit for example, the automatic control 115 specifies, threshold ATh to be 95%, which is higher than the automatic control reference threshold, and the recommendation threshold RTh to be 60%, which is higher than the recommendation reference threshold. At this time, the control-method specifying unit 115 specifies a device control method in which a recommendation to turn on the cooling of the air conditioner is made at 6:02. In this way, the control time is moved down further than that in the case of FIG. 7 in which the personality information is average. Increasing the threshold prevents execution of automatic control and decreases the frequency of device control.

For example, if openness is low in the personality information of the user, there is a tendency of the user to be annoyed about automatic control or a recommendation by the device control apparatus 110 because the user does not favor new experiences and variations in lifestyle. If the content of device control does not match the user's intent, the user may downgrade their assessment of the service by device control and terminate the use of the service by device control.

For example, if the emotional stability is low in the personality information of the user and the content of device control does not match the user's intent, the user may significantly downgrade their assessment of the service by device control and terminate the use of the service by device control.

For example, if diligence or self-control is high in the personality information of the user, there is not much room for transforming the user's behavior into a desired behavior because the user behaves in a planned manner in the first place. Therefore, in such a case, the target of device control is narrowed to something more certain, as described above, to reduce the possibility of the user feeling discomfort and increase the possibility of the user continuing the use of the service by device control.

A case will now be described in which the control-method specifying unit 115 determines a threshold in accordance with personality information of a user, to cause a recommendation to occur easily.

Figure 10:
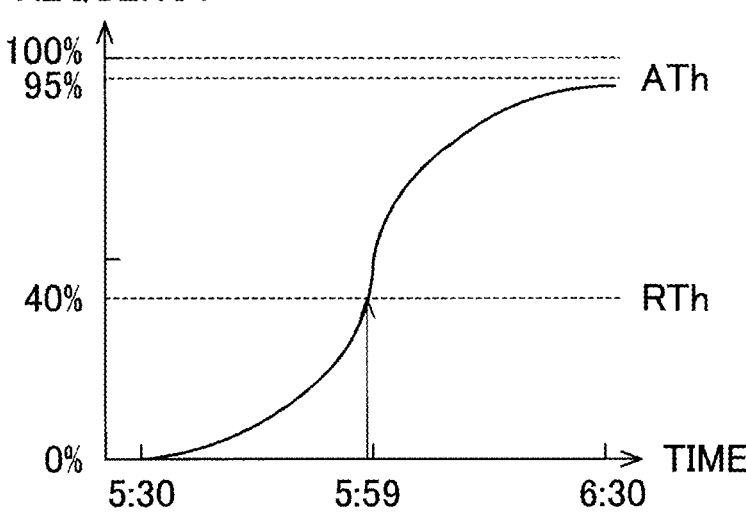
FIG. 10 is a graph explaining a fourth example of specifying a device control method.

FIG. 10 is a graph explaining a fourth example of specifying a device control method.

On the basis of personality information of a user, if causing a recommendation to occur easily improves the effect of a service provided by device control, e.g., if the user has high extraversion or high agreeableness, the control-method specifying unit 115 causes a recommendation to occur easily by changing the control threshold.

This is a case in which, for example, on the basis of personality information, extraversion is higher than a predetermined numerical range, or agreeableness is higher than a predetermined numerical range.

In such a case, the control-method specifying unit 115 specifies, for example, the automatic control threshold ATh to be 95%, which is higher than the automatic control reference threshold, and the recommendation threshold RTh to be 40%, which is lower than the recommendation reference threshold. At this time, the control-method specifying unit 115 specifies a device control method in which a recommendation to turn on the cooling of the air conditioner is made at 5:59. In this way, the frequency of recommendation increases, and the frequency of automatic control decreases in comparison with those in the case of FIG. 7 in which the personality information is average.

For example, if extraversion is high in the personality information of the user, there is a high tendency of the user to favor communication or conversation with the device control apparatus 110. For example, if agreeableness is high in the personality information of the user, there is a high tendency of the user to accept a recommendation when it does not greatly differ from the user's intent. Therefore, the frequency of recommendation can be increased as described above to enhance the effect of the service by device control without the user feeling discomfort. In contrast, that is, if the user has low extraversion or low agreeableness, the control-method specifying unit 115 may lower the frequency of recommendation.

A case will now be described in which the control-method specifying unit 115 specifies a threshold in accordance with personality information of the users when the device 101 is used by multiple users and personality information of the users has been acquired.

When only one user is registered to the control target device 101 or when the user can be specified as one user, the threshold may be determined in accordance with the personality information of the user.

When multiple users are registered to the control target device 101, and the current user cannot be specified, for example, the average of parameters representing personality information of the users may be obtained, and the threshold may be determined in accordance with the average. In place of the average of parameters, a representative value such as a median value, a maximum value, or a minimum value of the parameters may be preset.

When the frequency or time zone of use is preset for each user or when the sensor 102 can identify an individual, and the probability of the user being the current user can be quantified, the corresponding value may be weighted to obtain the average of parameters representing personality information, and the threshold may be determined in accordance with the value.

Therefore, if any of the parameters indicating "openness," "diligence," "extraversion," "agreeableness," "emotional stability," and "strength of self-control" falls outside a predetermined numerical range, the control-method specifying unit 115 specifies a negative weight value to lower the threshold by the parameters and a positive weight value to raise the threshold by the parameters, and determines a threshold by adding a weighted sum, which is obtained by multiplying the respective parameters of the personality information by the weight value, and adding the weighted sum to a reference threshold, the Here, threshold may be determined by applying a function, such as a logistic function, to the weighted sum and adding the result to the reference threshold. The weight value may be a predetermined constant value, or, in the case of a positive weight value, may be a value that increases as the parameter deviates from the predetermined numerical range and, in the case of a negative weight value, may be a value that decreases as the parameter deviates from the predetermined numerical range.

The device control method executed by the control unit 116 in step S14 in FIG. 5 will now be explained.

Figure 11:
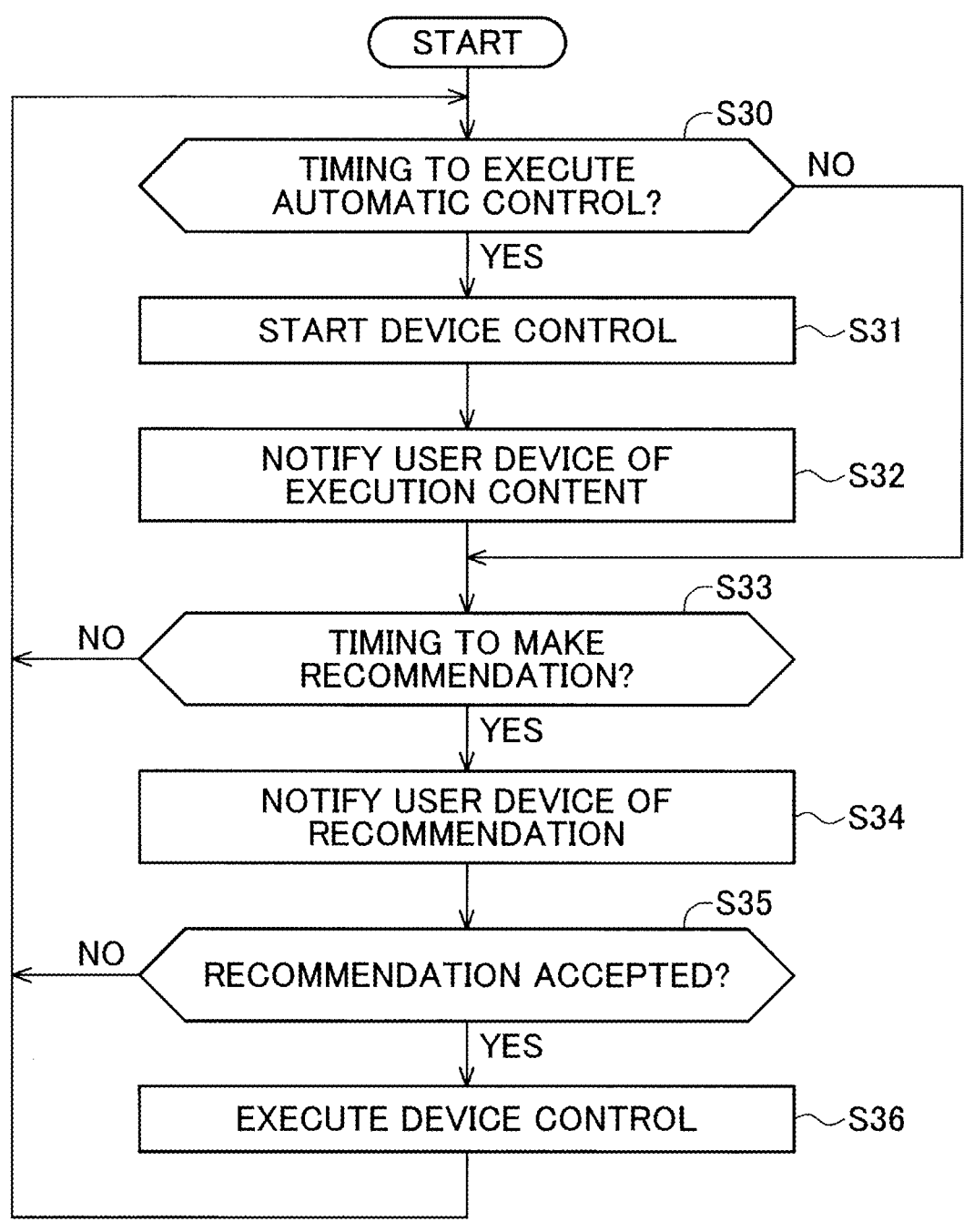
FIG. 11 is a flowchart illustrating an operation of a control unit.

FIG. 11 is a flowchart illustrating an operation of the control unit 116.

First, the control unit 116 determines whether or not it is a timing to execute automatic control (step S30). Even if it is the t time to execute automatic control specified by the control-method specifying unit 115, the control unit 116 determines that it is not the timing to execute control if the control is ineffective. The control is ineffective, for example, when the control content is to turn on the air conditioner cooling, but the user has already turned on the air conditioner cooling before this time. If it is the timing to execute automatic control (Yes in step S30), the process proceeds to step S31, and if it is not the timing to execute automatic control (No in step S30), the process proceeds to step S33.

In step S31, the control unit 116 performs a control target manipulation specified by the control-method specifying unit 115.

The control unit 116 notifies the user device 103 of the executed control content via the communication unit 111 (step S32). The processing then proceeds to step S33.

In step S33, the control unit 116 determines whether or not it is a timing to make a recommendation. Even if it is the time to make a recommendation specified by the control-method specifying unit 115, the control unit 116 determines that is the it not timing to make a recommendation if the recommendation is ineffective. The recommendation is ineffective, for example, when the recommendation content is to turn on the air conditioner cooling, but the user has already turned on the air conditioner cooling before this time. If it is the timing to make a recommendation (Yes in step S33), the process proceeds to step S34, and if it is not the timing to make a recommendation (No in step S33), the process returns to step S30.

In step S34, the control unit 116 recommends to the user via the user device 103 to perform the control target manipulation specified by the control-method specifying unit 115. For example, the control unit 116 sends a screen image recommending such a control target manipulation be performed to the user device 103 via the communication unit 111 and causes such a screen image to be displayed on the user device 103.

The control unit 116 then determines whether or not the user accepts to perform the recommended control target manipulation (step S35). For example, when the control unit 116 receives a notification indicating the acceptance of the control target manipulation from the user via the communication unit 111, the control unit 116 determines that the user has accepted to perform the recommended control target manipulation. In contrast, when the control unit 116 does not receive such a notification within a predetermined period or receives from the user a notification indicating that the control target manipulation is rejected via the communication unit 111, the control unit 116 determines that the user has not accepted to perform the recommended control target manipulation. If the user accepts to perform the recommended control target manipulation (Yes in step S35), the process proceeds to step S36, and if the user does not accept to perform the recommended control target manipulation (No in step S35), the process returns to step S30.

In step S36, the control unit 116 performs the control target manipulation specified by the control-method specifying unit 115. The process then returns to step S30.

According to the first embodiment described above, device control desirable to a user can be executed by executing the device control in accordance with the user's lifestyle pattern and the user's personality.

For example, when the user's personality favors the control of the device 101 by the device control apparatus 110, the control-method specifying unit 115 specifies a threshold to increase the frequency of control. In contrast, when the user's personality does not favor the control of the device 101 by the device control apparatus 110, a threshold is specified to decrease the frequency of control.

When the user's personality strongly controls the user's behavior, the control-method specifying unit 115 specifies a threshold to decrease the frequency of control. In contrast, when the user's personality weakly controls the user's behavior, the control-method specifying unit 115 specifies a threshold to increase the frequency of control.

When the user's personality favors dialogue, the control-method specifying unit 115 specifies a second threshold to increase the frequency of recommendation. In contrast, when the user's personality does not favor dialogue, the control-method specifying unit 115 specifies the second threshold to decrease the frequency of recommendation. In such a case, the first threshold may be raised so that automatic control is not readily executed, but the first embodiment is not limited to such an example.

In general, the more frequent device control is executed, the more likely the control includes that matching the user's intent, and thus less effort is required from the user; however, the control also includes that not matching the user's intent and thus causes the user to feel more discomfort. Here, the degree of discomfort when control does not match the user's intent varies depending on the user's personality. The degree of comfort or discomfort when control similar to the user's intent occurs also varies depending on the user's personality. Moreover, the desirability or intensity of the effect of reducing efforts also varies depending on the user's personality. According to the first embodiment, the user's satisfaction can be enhanced by determining the frequency of device control in accordance with personality.

The method of device control achieves the following effects by providing steps such as automatic control that does not require user acceptance and recommendation that requires user acceptance.

Control with a significantly high possibility of being what a user desires can be executed as automatic control to reduce the user's effort, such as accepting the control. When the possibility is not significantly high, the control may be recommended to request the user's acceptance, to reduce control that does not match the user's intent and discomfort caused by such control.

Furthermore, since the degree to which a user feels favorable about automatic control and recommendation depends on the user's personality, the user's satisfaction can be improved by changing the frequency of automatic control and recommendation depending on the user's personality.

According to the first embodiment, an adequate frequency of device control can be preset depending on the user's personality to enable execution of desired device control from an early stage in the service by device control. This eliminates the effort by a user to set a frequency of device control that matches the user through trial and error and the discomfort caused by such a process.

Second Embodiment

As illustrated in FIG. 1, a device control system 200 including a device control apparatus 210 according to the second embodiment includes devices 101, a sensor 102, a user device 103, and the device control apparatus 210.

The devices 101, the sensor 102, and the user device 103 of the device control system 200 according to the second embodiment are respectively the same as the devices 101, the sensor 102, and the user device 103 of the device control system 100 according to the first embodiment.

As illustrated in FIG. 1, the device control apparatus 210 according to the second embodiment includes a communication unit 111, a lifestyle-data storage unit 112, a lifestyle-pattern extracting unit 213, a personality-information acquiring unit 114, a control-method specifying unit 215, and a control unit 216.

The communication unit 111, the lifestyle-data storage unit 112, and the personality-information acquiring unit 114 of the device control apparatus 210 according to the second embodiment are respectively the same as the communication unit 111, the lifestyle-data storage unit 112, and the personality-information acquiring unit 114 of the device control apparatus 110 according to the first embodiment.

The lifestyle-pattern extracting unit 213 extracts a life-style pattern from the lifestyle data stored in the lifestyle-data storage unit 112.

The lifestyle pattern according to the second embodiment is a frequency with which events of a device 101 or the sensor 102 are linked under each condition.

For example, lifestyle data includes at least a history of multiple events related to a device 101, and the events include multiple manipulations of a function of the device 101. The lifestyle-pattern extracting unit 213 then refers to the lifestyle data to provide a plurality of permutations each obtained by extracting a first manipulation and a second manipulation from the plurality of manipulations, to calculate a frequency of the second manipulation following the preceding first manipulation being performed within a predetermined period, and to extract the frequency of each of the permutations as a lifestyle pattern.

The lifestyle data includes at least a history of multiple events related to the device 101 and the sensor 102, and the events include multiple manipulations of a function of the device 101 and detection of a predetermined target by the sensor 102. The lifestyle-pattern extracting unit 213 then refers to the lifestyle data to calculate the frequency of each of the manipulations being performed within a predetermined period on the basis of detection made by the sensor 102, and to extract the frequency calculated for each of the manipulations as the lifestyle pattern.

FIG. 12 is a table indicating an example of a lifestyle pattern according to the second embodiment.

In FIG. 12, the device 101A is an air conditioner, the device 101B is a television, and the sensor 102 is a human detection sensor.

FIG. 12 indicates the frequency of linked events such as an on-manipulation of air conditioner cooling, an off-manipulation of air conditioner cooling, an on-manipulation of television viewing, an off-manipulation of television viewing, and human detection by the human detection sensor.

Specifically, the vertical columns in FIG. 12 indicate triggering manipulations and operations. Here, an on-manipulation of air conditioner cooling, an off-air conditioner cooling, an on-manipulation of manipulation of television viewing, an off-manipulation of television viewing, and human detection by the human detection sensor are manipulations and operations that are triggers.

The horizontal rows in FIG. 12 indicate manipulations linked to the triggers. Here, an on-manipulation of air conditioner cooling, an off-manipulation of air conditioner cooling, an on-manipulation of television viewing, and an off-manipulation of television viewing are manipulations linked to triggers.

The numerical values in the table of FIG. 12 represent the frequency of a manipulation or an event linked to a triggering event occurring in a predetermined period after a manipulation or an operation serving as the triggering event has occurred in a specific period. The mark "-" in the table indicates that the frequency has not been calculated. The specific period is also referred to as a first period, and the predetermined period is also referred to as a second period.

Here, the specific period is from 5:00 a.m. to 10:00 a.m. on weekdays in the month up to the day of lifestyle pattern extraction, and the predetermined period is five minutes, but these may be changed as necessary.

For example, FIG. 12 indicates that if television viewing was turned off when the air conditioning was turned off in the specific period, the frequency of television viewing being turned on within the predetermined period of five minutes was 89%. Such a frequency is obtained by dividing the number of occurrences of a linked event in the predetermined period after a triggering event had occurred in the specific period by the number of possible occurrences of events linked to the triggering event that had occurred in the specified period.

A specific example of a possible occurrence of a linked event will now be described.

For example, it is presumed that a linked event is "television viewing being turned on." If television viewing is turned off when a triggering event occurs, this is a case in which the linked event could have occurred. In contrast, if television viewing is turned on when a triggering event occurs, this is a case in which the linked event could not have occurred.

It is preferred to divide the specific period into weekdays and holidays and calculate the frequencies of linked events for weekdays and holidays separately to establish lifestyle patterns because this enables different device control for weekdays and holidays in accordance with the lifestyle patterns of weekdays and holidays.

It is preferred to divide the specific period into time zones, such as morning and evening, and calculate the frequencies of linked events for the respective time zones to establish lifestyle patterns because this enables different device control for different time zones in accordance with the lifestyle patterns of the time zones.

Since the sensor 102 is not a target of manipulation by the user, the frequency of a sensor event linked to a trigger may be omitted from a lifestyle pattern, as in FIG. 12.

Also, linkage related to the same manipulation such as turning on and off a specific function of the same device 101 may be omitted from a lifestyle pattern as in FIG. 12 because such linkage is not used for control.

When the number of data items on which the frequency of linkage is based is small, the frequency may be omitted from the lifestyle pattern because it is unreliable. For example, the frequency of linkage may be omitted when the number of possible occurrences of events linked to a triggering event that had occurred within the specific period is less than a predetermined number (for example, five times). This can prevent inadequate control caused by unreliable values.

The control-method specifying unit 215 specifies a control method for a device 101 on the basis of a lifestyle pattern extracted by the lifestyle-pattern extracting unit 213 and personality information acquired by the personality-information acquiring unit 114.

For example, the control-method specifying unit 215 specifies a threshold based on personality information and compares the specified threshold with a lifestyle pattern to specify a control method for a device 101. In the second embodiment, the control-method specifying unit 215 specifies a triggering event and events linked to the triggering event as a device control method.

The control-method specifying unit 215 refers to the personality information to specify a threshold in accordance with the personality of the user and to specify the device control method when the frequency indicated by the lifestyle pattern exceeds the threshold, so that the device control method causes control related to the second manipulation to be executed when the preceding first manipulation is performed in a corresponding permutation.

Specifically, when a first threshold as a threshold is exceeded, the control-method specifying unit 215 specifies, as a device control method, a first device control method for automatically performing a following manipulation as control when a preceding manipulation of a corresponding permutation is performed, and when a second threshold as a threshold is exceeded, the control-method specifying unit 215 specifies a second device control method for recommending the following manipulation to be performed as control when the preceding manipulation of the corresponding permutation is performed.

The control-method specifying unit 215 refers to the personality information to specify a threshold in accordance with the personality of the user and to specify the device control method when the frequency indicated by the lifestyle pattern exceeds the threshold, the device control method causing control related to a corresponding manipulation to be executed when detection is made by the sensor 102.

Specifically, the control-method specifying unit 215 specifies, as a device control method, a first device control method for automatically performing a corresponding manipulation as control at the time of detection when a first threshold as a threshold is exceeded and specifies a second device control method for recommending a corresponding manipulation to be performed as control at the time of detection when a second threshold as a threshold lower than the first threshold is exceeded.

Details of the method for specifying a control method will be explained later.

The control unit 216 controls the devices 101 in accordance with a control method specified by the control-method specifying unit 215. In second embodiment, the control unit 216 performs a control method related to an event linked to a triggering event at a time when the triggering event specified by the control-method specifying unit 215 happens.

FIG. 13 is a table for explaining a first example of specifying a device control method on the basis of the frequency of the operation of the devices 101 being linked.

In FIG. 13, the devices 101 are an air conditioner and a television, and the sensor 102 is a human detection sensor. A case will be explained in which air conditioner cooling, television viewing, and detection by the human detection sensor are linked. The frequency of linkage was determined between 5:00 a.m. and 10:00 a.m. on weekdays.

Here, the personality information of the user is presumed to be average. This is a case in which, for example, all parameters in the personality information indicating openness, diligence, extraversion, agreeableness, emotional stability, and self-control are within a predetermined numerical range. The numerical range here may be the same for all parameters or different for each parameter.

The control-method specifying unit 115 determines, for example, an automatic control threshold for linking the devices 101 to be 90%, which is an automatic control reference threshold, and determines a recommendation threshold to link the devices to be 50%, which is a recommendation reference threshold.

In FIG. 13, the manipulation of turning off the air conditioner cooling linked to turning on television viewing exceeds the automatic control threshold.

The following manipulations exceed the recommendation threshold: an on-manipulation of television viewing linked to turning on air conditioner cooling, an off manipulation of television viewing linked to turning off air conditioner cooling, an off-manipulation of air conditioner cooling linked to turning off television viewing, and an off-manipulation of air conditioner cooling linked to detection made by the human detection sensor.

The control-method specifying unit 215 specifies a device control method that executes automatic control of a linked event when the frequency of the event being linked exceeds the automatic control threshold and sets the timing of the automatic control at the time of occurrence of a triggering event.

The control-method specifying unit 215 specifies a device control method that makes a recommendation of a linked event when the frequency of the event being linked exceeds the recommendation threshold and sets the timing of the recommendation at the time of occurrence of a triggering event.

In the example in FIG. 13, the control-method specifying unit 215 specifies a device control method for automatic control to turn on air conditioner cooling when television viewing is turned on, a device control method for recommending turning on television viewing when air conditioner cooling is turned on, a device control method for recommending turning off air conditioner cooling when television viewing is turned off, a device control method for recommending turning on air conditioner cooling when the human detection sensor makes a detection, and a device control method for recommending turning off television viewing when air conditioner cooling is turned off, during a period from 5:00 a.m. to 10:00 a.m. on weekdays. Similarly, a device control method may be specified on the basis of combinations of other devices 101 and the sensors 102 and frequencies determined in different periods.

A case will now be described in which the control-method specifying unit 215 specifies a threshold in accordance with personality information of a user, to cause device control to occur easily.

FIG. 14 is a table for explaining a second example of specifying a device control method on the basis of a frequency of operations of devices 101 being linked.

On the basis of personality information of a user, if causing device control to occur easily improves the effect of a service provided by the device control, e.g., if the user has high openness, high emotional stability, low diligence, or low self-control, the control-method specifying unit 215 causes the device control to occur easily by lowering the control threshold.

This is a case in which, for example, on the basis of personality information, openness is higher than a predetermined numerical range, emotional stability is higher than a predetermined numerical range, diligence is lower than a predetermined numerical range, or self-control is lower than a predetermined numerical range.

In such a case, the control-method specifying unit 215 specifies, for example, the automatic control threshold to be 80%, which is lower than an automatic control reference threshold, and the recommendation threshold to be 40%, which is lower than a recommendation reference threshold. In such a case, the device control method specified by the control-method specifying unit 215 includes an additional device control method for recommending turning television viewing ON when the human detection sensor makes a detection, as compared to the case in FIG. 13 where personality information is average. The device control method for recommending television viewing ON when air conditioner cooling ON occurs is changed to a device control method for executing automatic control.

In this way, lowering the threshold increases the frequency of device control. Recommendation is changed to automatic control to promote automation.

A case will now be described in which the control-method specifying unit 215 specifies a threshold according to personality information of a user, thereby making device control not occur easily.

FIG. 15 is a table to illustrate a third example of specifying a device control method on the basis of the frequency of the operation of the device 101 to be linked.

When the effect of service by device control improves by making device control not occur easily in the personality information of a user, for example, when the openness of the user is low, the emotional stability is low, the diligence is high, or the self-control is high, the control-method specifying unit 215 makes device control not to occur easily by increasing the threshold of control.

This is a case in which, for example, on the basis of personality information, openness is lower than a predetermined numerical range, emotional stability is lower than a predetermined numerical range, diligence is higher than a predetermined numerical range, or self-control is higher than a predetermined numerical range.

In such a case, the control-method specifying unit 215 specifies, for example, the automatic control threshold to be 95%, which is higher than an automatic control threshold, reference and the recommendation threshold to be 60%, which is higher than a recommendation reference threshold. In such a case, the device control method specified by the control-method specifying unit 215 eliminates the device control method for recommending television viewing OFF when air conditioner cooling OFF occurs, as compared to the case in FIG. 13 where personality information is average. The device control method of automatic control for turning on air conditioner cooling when television viewing is turned on is changed to a device control method for recommendation.

In this way, raising the threshold decreases the frequency of device control. Automatic control is changed to recommendation to suppress automation.

A case will now be described in which the control-method specifying unit 215 determines a threshold according to personality information of a user, thereby making a recommendation easily generated.

FIG. 16 is a table illustrating a fourth example of specifying a device control method on the basis of the frequency of the operation of the device 101 to be linked.

On the basis of personality information of a user, if causing a recommendation to occur easily improves the effect of a service provided by device control, e.g., if the user has high extraversion or high agreeableness, the control-method specifying unit 115 causes a recommendation to occur easily by changing the control threshold.

This is a case in which, for example, on the basis of personality information, extraversion is higher than a predetermined numerical range, or agreeableness is higher than a predetermined numerical range.

In such a case, the control-method specifying unit 215 specifies, for example, the automatic control threshold to be 95%, which is higher than an automatic control reference threshold, and the recommendation threshold to be 40%, which is lower than a recommendation reference threshold. In such a case, the device control method specified by the control-method specifying unit 215 includes an additional device control method for recommending turning on television viewing when the human detection sensor makes a detection, as compared to the case in FIG. 13, where personality information is average. The device control method of automatic control for turning on air conditioner cooling when television viewing is turned on is changed to a device control method for making a recommendation.

Changing the threshold in this way increases the frequency of recommendations.

In the second embodiment, if any of the parameters indicating "openness," "diligence," "extraversion," "agreeableness," "emotional stability," and "strength of self-control" falls outside a predetermined numerical range, the control-method specifying unit 215 specifies a negative weight value to lower a reference threshold by the parameters and a positive weight value to raise the reference threshold by the parameters, and determines a threshold by adding a weighted sum, which is obtained by multiplying the respective parameters of the personality information by the weight value, and adding the weighted sum to the reference threshold. Here, the threshold may be determined by applying a function, such as a logistic function, to the weighted sum and adding the result to the reference threshold. The weight value may be a predetermined constant value, or, in the case of a positive weight value, may be a value that increases as the parameter deviates from the predetermined numerical range and, in the case of a negative weight value, may be a value that decreases as the parameter deviates from the predetermined numerical range.

According to the second embodiment described above, device control desirable to a user can be executed by executing the device control in accordance with the user's lifestyle pattern and the user's personality.

While the lifestyle pattern of the first embodiment described above is the frequency of a function of each device 101 being used under each condition such as time, the lifestyle pattern of the second embodiment is the frequency with which events of a device 101 or the sensor 102 are linked under each condition; however, the lifestyle pattern of the first and second embodiments is not limited to the above examples. For example, a lifestyle pattern may be extracted from a frequent pattern tree by preparing an episode creation rule, creating episode data on the basis of the episode creation rule, and creating a frequent pattern tree from the episode data, on the basis of the method disclosed in Patent Literature 1.

The lifestyle pattern is not limited to being extracted from user's lifestyle data alone. For example, the lifestyle-pattern extracting units 113 and 213 may preliminarily hold lifestyle patterns referring to general users. The lifestyle-pattern extracting units 113 and 213 may acquire and hold lifestyle patterns extracted from the lifestyle data of another user.

Although the first and second embodiments have been described above, the disclosure is not limited to these embodiments. Even when a lifestyle pattern is extracted by a different method, it is possible to achieve the same effect as that of the first or second embodiment by determining the threshold for determining a lifestyle pattern to be subjected to control execution on the basis of personality information when the device control method is specified.

DESCRIPTION OF REFERENCE CHARACTERS

100, 200 device control system; 101 device; 102 sensor; 103 user device; 110, 210 device control apparatus; 111 communication unit; 112 lifestyle-data storage unit; 113, 213 lifestyle-pattern extracting unit; 114 personality-information acquiring unit; 115, 2 control-method specifying unit; 116, 216 control unit.

What is claimed is:

1. A device control apparatus comprising:
processing circuitry
to acquire personality information indicating personality traits of a user including at least one of openness, diligence, extraversion, agreeableness, emotional stability, and strength of self-control;

to specify a device control method based on the personality information and a lifestyle pattern of the user that indicates a history of use of the device during weekdays and holidays, the device control method being a control method for a device used by the user; and to control the device in accordance with the device control method, wherein the processing circuitry further stores lifestyle data indicating a history of events including a plurality of manipulations of a function of the device, extracts the lifestyle pattern from the lifestyle data, and calculates a frequency of each of the manipulations being performed during each of a plurality of predetermined time zones by referring to the lifestyle data and extracts the frequency of each of the manipulations during the each of the predetermined time zones as the lifestyle pattern.

2. The device control apparatus according to claim 1, wherein the processing circuitry specifies a threshold in accordance with the personality traits of the user by referring to the personality information and specifies the device control method when the frequency exceeds the threshold, the device control method causing control related to a corresponding manipulation to be executed during a corresponding time zone.

3. The device control apparatus according to claim 2, wherein the processing circuitry specifies a first device control method as the device control method when a first threshold serving as the threshold is exceeded and specifies a second device control method as the device control method when a second threshold serving as the threshold is exceeded, the second threshold being lower than the first threshold, the first device control method causing the corresponding manipulation to be automatically performed as the control, the second device control method recommending performing the corresponding manipulation as the control.

4. The device control apparatus according to claim 3, wherein, the personality information includes an element capable of specifying whether or not the personality traits favor conversation, and the processing circuitry specifies the second threshold to increase the frequency of the recommendation when the personality traits favor conversation and specifies the second threshold to decrease the frequency of the recommendation when the personality traits do not favor conversation.

5. The device control apparatus according to claim 2, wherein, the personality information includes an element capable of specifying whether or not the personality traits favor control of the device by the device control apparatus, and the processing circuitry specifies the threshold to increase the frequency of the control when the personality traits favor control of the device by the device control apparatus and specifies the threshold to decrease the frequency of the control when the personality traits do not favor control of the device by the device control apparatus.

6. The device control apparatus according to claim 2, wherein, the personality information includes an element capable of specifying whether the personality traits strongly or weakly control a behavior of the user, and the processing circuitry specifies the threshold to decrease the frequency of the control when the personality traits strongly control the behavior of the user and specifies the threshold to increase the frequency of the control when the personality traits weakly control the behavior of the user.

7. The device control apparatus according to claim 1, wherein the processing circuitry provides a plurality of permutations each obtained by extracting a first manipulation and a second manipulation from the plurality of manipulations by referring to the lifestyle data, calculates a frequency of the second manipulation following the preceding first manipulation being performed within a predetermined period by referring to the lifestyle data, and extracts the frequency of each of the permutations as a lifestyle pattern.

8. The device control apparatus according to claim 7, wherein the processing circuitry specifies a threshold in accordance with the personality traits of the user by referring to the personality information and specifies the device control method when the frequency exceeds the threshold, the device control method causes control related to the second manipulation to be executed when the preceding first manipulation is performed in a corresponding permutation.

9. The device control apparatus according to claim 8, wherein the processing circuitry specifies a first device control method as the device control method when a first threshold serving as the threshold is exceeded and specifies a second device control method as the device control method when a second threshold serving as the threshold is exceeded, the first device control method causing the second manipulation to be automatically performed when the preceding first manipulation is performed in the corresponding permutation as the control, the second device control method recommending the second manipulation to be performed when the preceding first manipulation is performed in the corresponding permutation as the control.

10. The device control apparatus according to claim 8, wherein, the personality information includes an element capable of specifying whether or not the personality traits favor control of the device by the device control apparatus, and the processing circuitry specifies the threshold to increase the frequency of the control when the personality traits favor control of the device by the device control apparatus and specifies the threshold to decrease the frequency of the control when the personality traits do not favor control of the device by the device control apparatus.

11. The device control apparatus according to claim 8, wherein, the personality information includes an element capable of specifying whether the personality traits strongly or weakly control a behavior of the user, and the processing circuitry specifies the threshold to decrease the frequency of the control when the personality traits strongly control the behavior of the user and specifies the threshold to increase the frequency of the control when the personality traits weakly control the behavior of the user.

12. The device control apparatus according to claim 1, wherein, the events further include detection of a predetermined target by a sensor, and the processing circuitry stores data corresponding to the detection of the predetermined target by the sensor as part of the lifestyle data.

13. The device control apparatus according to claim 12, wherein the processing circuitry specifies a threshold in accordance with the personality traits of the user by referring to the personality information and specifies the device control method when the frequency exceeds the threshold, the device control method causing control related to a corresponding manipulation to be executed when the detection is made.

14. The device control apparatus according to claim 13, wherein the processing circuitry specifies a first device control method as the device control method when a first threshold serving as the threshold is exceeded and specifies a second device control method as the device control method when a second threshold serving as the threshold is exceeded, the second threshold being lower than the first threshold, the first device control method causing the corresponding manipulation to be automatically performed as the control when the detection is made, the second device control method recommending performing the corresponding manipulation as the control when the detection is made.

15. The device control apparatus according to claim 13, wherein, the personality information includes an element capable of specifying whether or not the personality traits favor control of the device by the device control apparatus, and the processing circuitry specifies the threshold to increase the frequency of the control when the personality traits favor control of the device by the device control apparatus and specifies the threshold to decrease the frequency of the control when the personality traits do not favor control of the device by the device control apparatus.

16. The device control apparatus according to claim 13, wherein, the personality information includes an element capable of specifying whether the personality traits strongly or weakly control a behavior of the user, and the processing circuitry specifies the threshold to decrease the frequency of the control when the personality traits strongly control the behavior of the user and specifies the threshold to increase the frequency of the control when the personality traits weakly control the behavior of the user.

17. A non-transitory computer-readable medium that stores therein a program that causes a computer to execute processes of:

acquiring personality information indicating personality traits of a user including at least one of openness, diligence, extraversion, agreeableness, emotional stability, and strength of self-control;

specifying a device control method from the personality information and a lifestyle pattern of the user that indicates a history of use of the device during weekdays and holidays, the device control method being a control method for a device used by the user; and controlling the device in accordance with the device control method, wherein the process further includes storing lifestyle data indicating a history of events including a plurality of manipulations of a function of the device, extracting the lifestyle pattern from the lifestyle data, and calculating a frequency of each of the manipulations being performed during each of a plurality of predetermined time zones by referring to the lifestyle data and extracts the frequency of each of the manipulations during the each of the predetermined time zones as the lifestyle pattern.

18. A device control method comprising:

acquiring personality information indicating personality traits of a user including at least one of openness, diligence, extraversion, agreeableness, emotional stability, and strength of self-control;

specifying a device control method from the personality information and a lifestyle pattern of the user that indicates a history of use of the device during weekdays and holidays, the device control method being a control method for a device used by the user; and controlling the device in accordance with the device control method, wherein the device control method further includes storing lifestyle data indicating a history of events including a plurality of manipulations of a function of the device, extracting the lifestyle pattern from the lifestyle data, and calculating a frequency of each of the manipulations being performed during each of a plurality of predetermined time zones by referring to the lifestyle data and extracts the frequency of each of the manipulations during the each of the predetermined time zones as the lifestyle pattern.

* * * * *